(12) United States Patent  
Gudmundsson et al.

(10) Patent No.: US 7,168,390 B2  
(45) Date of Patent: Jan. 30, 2007

(54) MILK SAMPLING APPARATUS AND METHOD

(75) Inventors: Mats Gudmundsson, Södertälje (SE); Sten Mellberg, Stockholm (SE)

(73) Assignee: Delaval Holding AB, Tumba (SE)

( * ) Notice: Subject to any disclaimer, the term of this patent is extended or adjusted under 35 U.S.C. 154(b) by 738 days.

(21) Appl. No.: 10/240,394

(22) PCT Filed: Mar. 28, 2001

(86) PCT No.: PCT/SE01/00678

§ 371 (c)(1), (2), (4) Date: Sep. 30, 2002

(87) PCT Pub. No.: WO01/74151

PCT Pub. Date: Oct. 11, 2001

(65) Prior Publication Data

US 2003/0143748 A1    Jul. 31, 2003

(51) Int. Cl.  
*A01J 5/00*      (2006.01)  
*A01J 7/00*      (2006.01)

(52) U.S. Cl. .......................... 119/14.02; 119/14.18

(58) Field of Classification Search ............ 119/14.02, 119/14.08, 14.14, 14.18; 141/130, 284  
See application file for complete search history.

(56) References Cited

U.S. PATENT DOCUMENTS

| | | | | |
|---|---|---|---|---|
| 4,102,649 A | * | 7/1978 | Sasaki | 366/114 |
| 4,224,278 A | * | 9/1980 | Hogen Esch | 422/65 |
| 4,636,476 A | | 1/1987 | Brunt et al. | |
| 4,914,966 A | * | 4/1990 | White, Jr. et al. | 73/863.01 |
| 5,259,672 A | | 11/1993 | Rowe | |
| 5,479,969 A | * | 1/1996 | Hardie et al. | 141/130 |
| 5,843,376 A | * | 12/1998 | Ishihara et al. | 422/64 |

FOREIGN PATENT DOCUMENTS

| | | |
|---|---|---|
| EP | 0494066 | 7/1992 |
| EP | 0564023 | 10/1993 |
| EP | 0749681 | 12/1996 |
| GB | 2030110 | 4/1980 |

OTHER PUBLICATIONS

European Notice of Opposition dated Oct. 27, 2005.  
Margarete Rapp et al., "Neuentwicklung von flüssigen Konservierungsmitteln für milchproben," *dmz deutsche molkereizeitung*, 1984, pp. 1264-1272.  
Olivier Leray, "Mémento sur la Conservation des ÉChantillons," *CECALAIT*, Nov. 1983, pp. 1-13.  
M.C. van der Haven et al., "Melkwinning," *Handboek*, Aug. 1996, pp. 117-118.

* cited by examiner

*Primary Examiner*—Robert P. Swiatek  
(74) *Attorney, Agent, or Firm*—Harness, Dickey & Pierce, P.L.C.

(57) ABSTRACT

A milk sampling apparatus for use with an automated milking system. The apparatus may include a cassette wherein milk sample collecting elements may be placed, and at least one filling member capable of being placed above a selected one of the milk sample collecting elements by a positioning system, and capable of bringing a milk sample, representatively taken from milk yielded during the milking of an animal by the automated milking system, in the selected one of the milk sample collecting elements. Further, the milk sampling apparatus may include an agitating device, such as a shaking table, for agitating the milk sample.

34 Claims, 5 Drawing Sheets

MILK SAMPLING APPARATUS AND METHOD

TECHNICAL FIELD OF THE INVENTION

The present invention generally relates to dairy farm machine milking and to milk sampling related thereto.

Particularly, the invention relates to a milk sampling apparatus for use with an automated milking system and to a method for sampling of milk from said automated milking system.

DESCRIPTION OF RELATED ART AND BACKGROUND OF THE INVENTION

When milking an animal by using an automated milking system, the milk is drawn from the teats of the animal by means of teat cups connected to vacuum. The milk is drawn through a milk tube and into a flow meter wherein the amount of milk is measured. The milk is further transported to a storing tank or similar wherein it is stored together with milk from other animals while waiting for a milk lorry to collect it.

On regular time basis, e.g. once a month, a sample of the milk from each animal is taken, which sample is typically sent to a laboratory for analysis, in which various parameters such as contents of fat, protein, cell, and urea are examined. It is expensive to implement the analysis at the milk sampling device and further, the laboratory equipment necessary is space demanding, thus samples are typically taken and sent to a laboratory. Possibly, some kind of simpler measurements could be introduced at the milk sampling device.

The milk sampling is typically performed in connection with milking of the animals by employing a milk sampling device provided with a fixed or removable cassette wherein milk test tubes can be placed, and with a filling member connected to the milking system and capable of filling the respective tubes with milk from the respective animals. When all the tubes are filled they are removed from the milk sampling device, either manually one by one, or by means of removing the complete cassette, and sent to the laboratory.

The laboratory equipment is adapted to the cassettes and test tubes that are used by the farmers served by that laboratory. Further, laboratory equipment, cassettes and test tubes, vary quite much from country to country.

Further, the sample tubes are typically prepared with a preservative prior to milk sampling, which preservative shall restrain the milk from turning to sour before the samples have been delivered to the laboratory and been analyzed. This preservative is to be dissolved in the milk, which typically takes a period of time, during which the increase of bacteria in the milk speeds up, whereby the risk that the milk turns to sour increases.

One prior art milk sampling device is disclosed in EP 0 564 023 A1 (LELY/MAASLAND). This device is provided with a cassette formed as a rotating box in which, along its circumference, milk sample collecting elements can be arranged. The filling member is disposed in a fixed position, while the collecting elements can be placed successively under the filling member. The filling member is further provided with a vertically movable type of injection needle to be inserted into the collecting elements. In this construction, the cassette and the injection needle have to be moved synchronously, which requires specific measures to be taken.

Besides, in case of a relatively large number of collecting elements, the space in the box is insufficiently utilized. Therefore, the cassette occupies relatively much space, which in view of the extensive equipment present in milking systems of today, is experienced as a drawback.

Another prior art milk sampling device is depicted in EP 0 749 681 A1 (LELY/MAASLAND). This device is provided with a removable cassette in which milk sample collecting elements can be placed, and at least one filling member capable of being placed successively above various collecting elements and bringing milk samples, taken from milk provided by an automatic milking machine, to the respective collecting elements. Guide means is provided for supporting the filling member such that the filling member is moved, by successively increasing and decreasing the distance between the guide means and the cassette, from a position above a collecting element to an adjacent position above a nearby situated collecting element. In such manner the filling member may step from collecting element to collecting element along a predetermined fixed zigzag formed closed path.

This device has a simple design, but the movement of the filling member is not flexible since it is determined by said fixed path. This may be a major drawback if a single collecting element is to be used for collecting a second non-consecutive sample, e.g. for sampling a cow a second time a number of hours later, as the guide means may have to step through a relatively long path before reaching the collecting element in question.

A further drawback of both these prior art milk sampling devices is that they are designed to fit only one cassette size. As there exist different standards of cassettes and sample collecting elements in different countries a device has to be manufactured in various designs if it is to be put on several markets.

Further, there is a certain risk of mixing samples at the milking farm, during transport, or at the laboratory since the individual sample collecting elements are only identified through their respective positions in the cassette.

If the individual sample collecting elements are removed from the cassette of the milk sampling device and placed in other cassette or box for being dispatched to the laboratory, this risk of mixing samples is considerably increased as well as such an approach is time consuming, labor intensive and thus costly.

Further, the above-mentioned documents neither address the apparent problem that the milk samples may turn to sour before reaching the laboratory nor discuss the dissolving of a preservative in the milk samples.

SUMMARY OF THE INVENTION

Accordingly, it is an object of the present invention to provide a milk sampling apparatus and method, which avoid at least some of the problems associated with prior art devices.

It is a particular object of the invention to provide a milk sampling apparatus and method, in which milk samples can be preserved by adding a preservative to them.

It is in this respect a further object of the invention to provide such milk sampling apparatus and method, in which the preservative and the milk can be mixed appropriately.

It is yet a further object of the invention to provide a milk sampling apparatus and method, which are flexible and which can provide for a variable filling member movement capability.

It is still a further object of the invention to provide a milk sampling apparatus and method, in which cassettes of various designs and sizes can be placed.

It is yet a further object of the invention to provide a milk sampling apparatus and method, which are capable of being adaptable for two-way communication with an automated milking system.

It is still a further object of the invention to provide a milk sampling apparatus and method, which are effective, fast, accurate, reliable, safe, easy to use, and of low cost.

These objects among others are, according to the present invention, attained by a milk sampling apparatus and method that inter alia comprise agitation of milk samples representatively taken from milk yielded during the milking of animals by means of an automated milking system.

The milk sampling apparatus comprises a cassette wherein milk sample collecting elements are placed, and a filling member capable of being placed above the milk sample collecting elements by means of a flexible positioning system, and capable of bringing milk samples, into said milk sample collecting elements.

Thus, the agitation of the milk samples comprises preferably movement of the collecting elements that contain the milk samples or of the complete cassette. In the latter case the milk sampling apparatus may comprise a shaking table for shaking of the cassette. Preferably, in such instance, the shaking table is arranged on a chassis by means of elastic isolator support means and is arranged to be shaken by means of a motor rotating an eccentric disk.

A preservative can be added to the milk sample or the milk sample collecting element can be prepared with a preservative prior to milk sampling.

Preferably, agitation is performed subsequent to each taking of a milk sample.

Further features and embodiments of the present invention are found in the appended claims.

A major advantage of the invention is that it provides for a fast agitating of the milk samples, which increases the dissolving rate of any preservative added to the milk samples. Such approach provides for an extended use of the milk sample apparatus.

A further advantage of the invention is the usability with a large range of cassette and sample collecting element designs and sizes, i.a. due to the variable movement capability of the flexible filling member and the use of a flexible insert.

Further characteristics of the invention and advantages thereof will be evident from the following detailed description of embodiments of the invention.

BRIEF DESCRIPTION OF THE DRAWINGS

The present invention will become more fully understood from the detailed description of embodiments of the present invention given hereinbelow and the accompanying FIGS. 1–4, which are given by way of illustration only, and thus are not limitative of the present invention.

DETAILED DESCRIPTION OF EMBODIMENTS

In the following description, for purposes of explanation and not limitation, specific details are set forth, such as particular techniques and applications in order to provide a thorough understanding of the present invention. However, it will be apparent to one skilled in the art that the present invention may be practiced in other embodiments that depart from these specific details. In other instances, detailed descriptions of well-known methods and apparatuses are omitted so as not to obscure the description of the present invention with unnecessary details.

Figure 1:
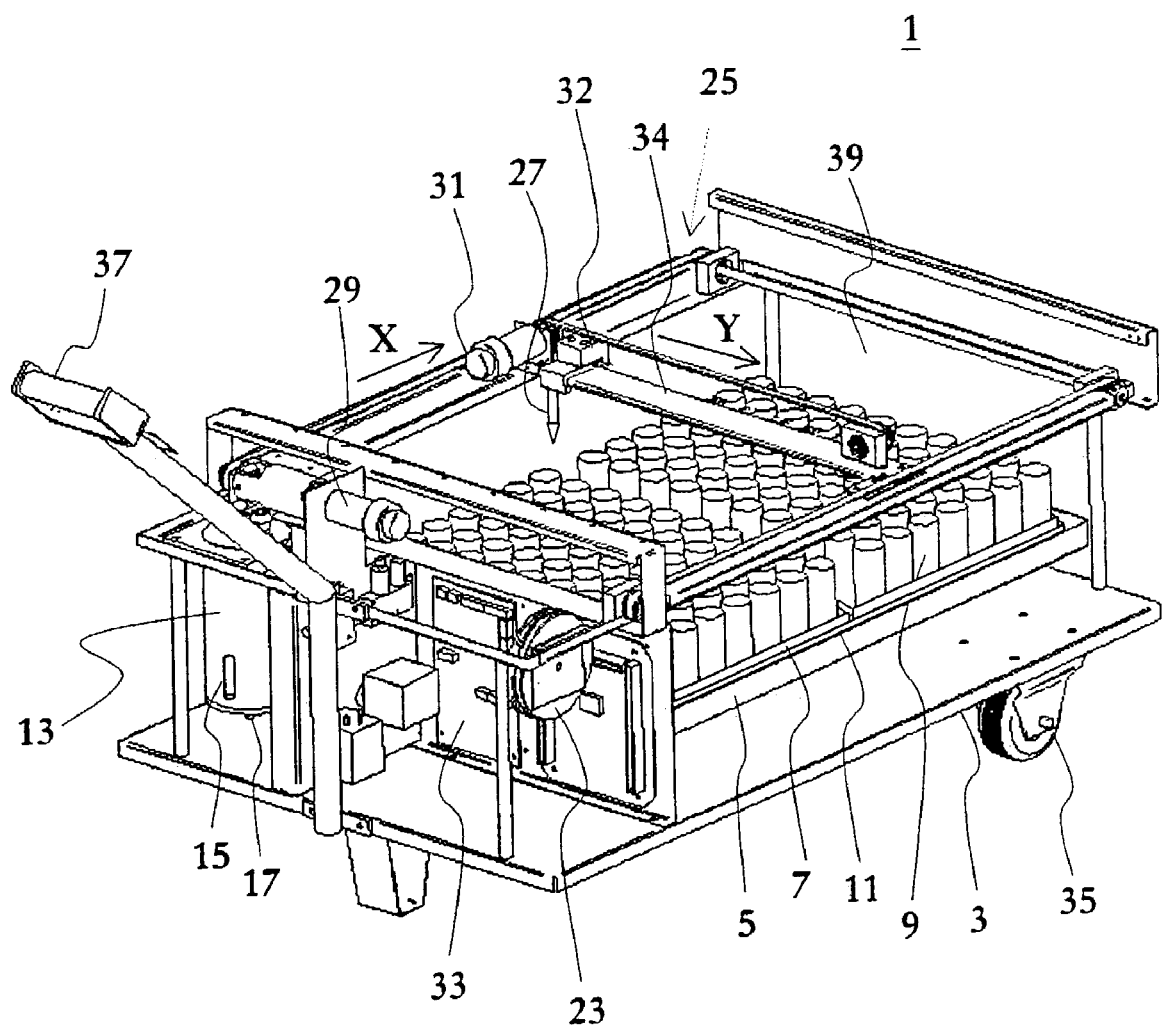
FIG. 1 displays schematically an embodiment of a milk sampling apparatus according to the present invention.

Referring to FIG. 1 an embodiment of a milk sampling apparatus 1 according to the present invention comprises a stainless steel chassis 3 at which a shaking or vibrating table 5 is mounted. At table 5 one, or preferably two, cassettes 7 are removably mounted, in which cassette milk sample collecting elements or tubes 9 are placed. Tubes 9 are arranged vertically with their openings pointing upwards.

A rubber sheet or insert 11 may be provided at the upper surface of table 5 having a punched through opening, wherein cassette(s) 7 can be arranged. The opening is made such that a close fit between cassette(s) 7 and rubber sheet 11 is obtained. Sheet 11 is preferably about 25 mm thick and may be of any other suitable material such as e.g. steel. The provision of rubber sheet 11 allows for possibilities to tailor-make the sampling apparatus to fit with a particular cassette or a particular practice or standard.

The lateral dimensions of chassis 3, shaking table 5 and rubber sheet 11 are preferably such that there is room for two conventional German sample cassettes, which are the largest cassettes the present inventors have found on the market. In such a cassette there is room for 70 sample tubes and 140 sample tubes will probably be sufficient in order to handle 50 milking animals during a period of 24 hours if each animal yields one sample per milking. If a single sample tube may be used more than one time for a given animal that presents for milking during the 24 hours interval, the milk sample device can handle even more animals or, alternatively, the number of sample tubes may be reduced.

Further, the milk sampling apparatus comprises a collection vessel 13, which can be arranged in fluid connection with a milk passage, e.g. vessel or conduit, of an automated milking station to which the milk sampling apparatus is connectable via adjustment of a valve (not shown in FIG. 1).

Preferably, collection vessel 13 is by means of a vacuum supplied hose connected to a likewise vacuum supplied flow meter of the automated milking system, through which flow meter all milk as drawn from a milking animal is passed. A representative milk amount, typically about 2% (corresponding to about half a liter) of the total milk amount from a milking, is by way of gravity flowed into collection vessel 13 when a sample is to be taken. The hose has in a preferred embodiment an inner diameter of 10 mm and a thickness of material of about 3 mm.

Collection vessel 13 is also connected to a source of compressed air via a pressure regulator (not shown in FIG. 1) for the supply of air.

Further, two different discharge outlets are arranged at different heights of collection vessel 13, of which the upper outlet 15 is connected to a discharge line (not shown in FIG. 1) and the lower outlet 17, being located at bottom of vessel 13, is via a conduit connected to a hose (not shown in FIG. 1) arranged in a spring biased reel 23.

The milk sampling apparatus of FIG. 1 comprises further a servo-operated XY-positioning system or table 25 arranged parallel with and above cassette(s) 7. XY-positioning system 25 is a device adapted for flexible positioning of a filling member 27 above a selected one of the plurality of sample tubes in cassette(s) 7. XY-positioning system 25 comprises two servo systems 29, 31, of which a first moves an arm 34 in the X-direction such that the position of the arm is proportional to a first provided signal value (e.g. a voltage) or a first provided number of pulses. The filling member, being connected to the hose of hose reel 23, is mounted on a runner 32 that is movable along the arm in the Y-direction such that the position of runner 32 and filling member 27 is proportional to a second provided signal value (e.g. voltage) or a second provided number of pulses. The operation is thus similar to a conventional XY recorder.

A processing means 33 is provided for two-way communication with the automated milking system, which will be further depicted below with reference to FIG. 3. Processing means 33 controls the position of the filling member as well as all valves included in the apparatus.

All valves are preferably of hose clamping kind such that no pockets or spaces, where dirt and bacteria may settle, exists. The hose clamps are preferably electromechanical, wherein the hose is pinched by means of a spring and opened by means of an electromagnet. Pneumatic valves may alternatively be used.

The milk sampling apparatus may preferably be provided with wheels 35 and a handle 37, such that the apparatus may easily be transported by the farmer. The apparatus comprises also a cover 39 to protect from dirt, the cover being preferably transparent such that the operation of the apparatus may be observed by the farmer. Furthermore, the apparatus is designed such that the distance between the cassette and the floor is large and the handling of the sample tubes takes place from above. In such an instance the risk of contamination of the samples is minimized and a good hygiene is safeguarded.

Next, with reference to FIGS. 2a–d, four different designs of the XY-positioning system as being part of the milk sampling apparatus of FIG. 1 will briefly be discussed.

Figure 2A:
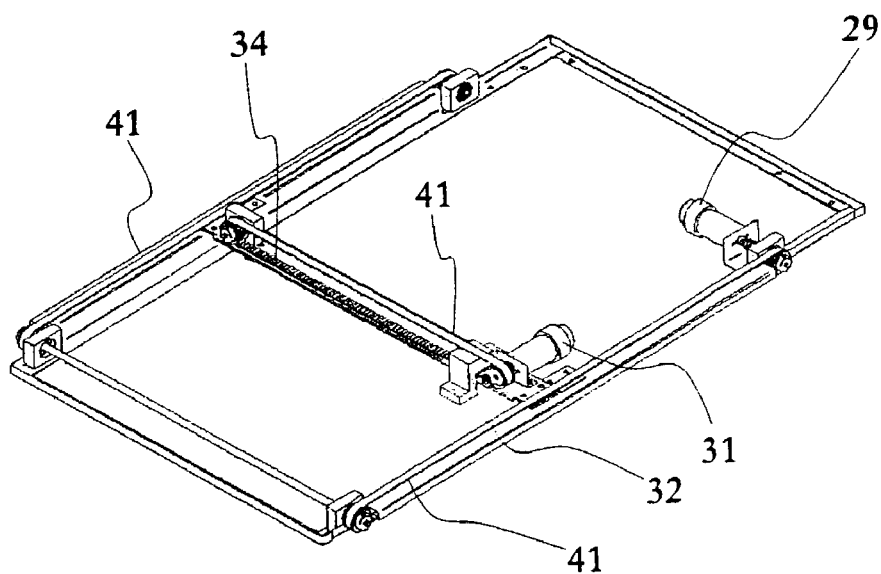
FIGS. 2a–d illustrate four different embodiments of an XY-positioning system as being included in the milk sampling apparatus of FIG. 1.

A simple and low cost implementation of the transmission of force, as illustrated in FIG. 2a, is the use of synchronous transmission or drive belts 41. Using such transmission a reliable design, which require no maintenance, is achieved. The precision is not excellent, but acceptable for the present purpose. The force the transmission has to cope with, is only the tension force from the hose reel and any occurring friction.

Figure 2B:
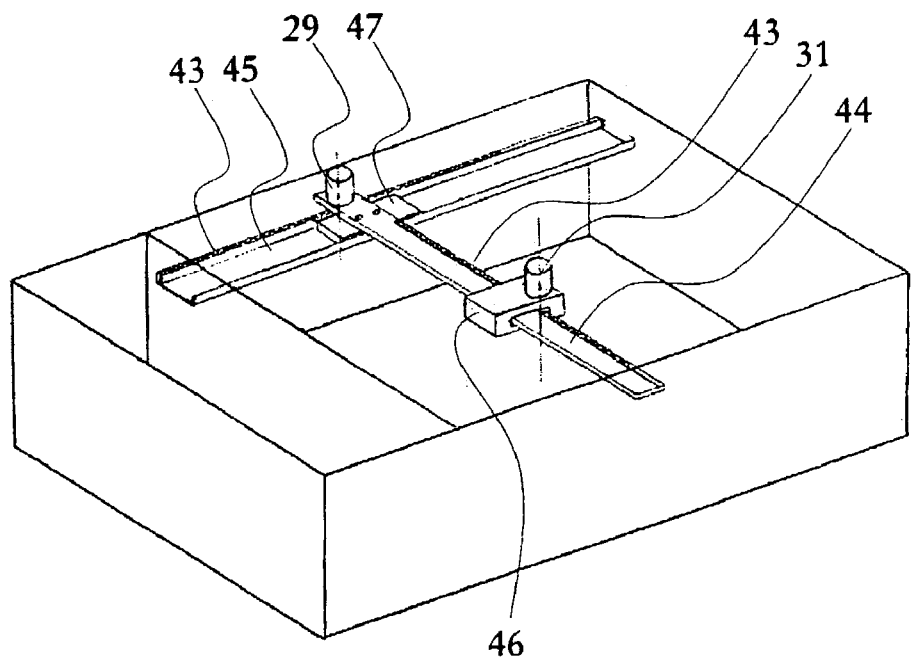

An alternative implementation, shown in FIG. 2b, uses linear rails with runners. The transmission of the runners is realized by means of gear racks 43 along rails 44, 45 and motors 29, 31 mounted on respective runners 46, 47, wherein rail 44 is firmly mounted on runner 47. The performance of this implementation would be similar to that of the implementation of FIG. 2a. One drawback using this implementation, however, is that more cords must be flexible and movable.

Figure 2C:
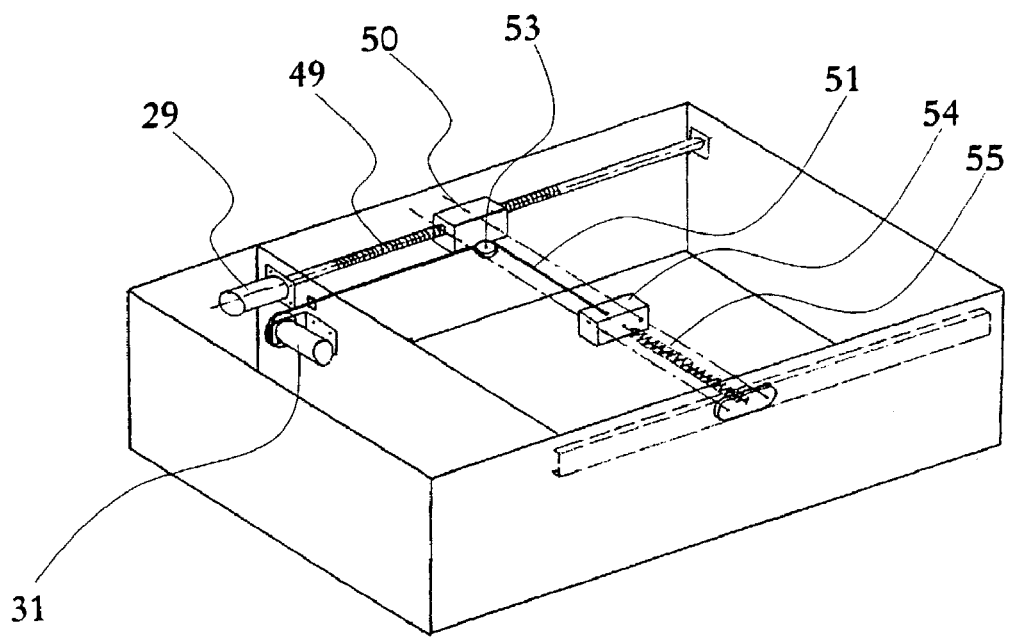

A further alternative, shown in FIG. 2c, is implementing a rotatable trapezoid threaded screw 49 and a runner or nut 50 for transmission, gearing, and load carrying in the X direction, said runner being prevented from being rotated. The movement in the Y direction is realized by a wire 51, which is journalled 53 at runner 50 and is attached to a further runner 54, which in turn is attached to a biased slidable spring 55. In this alternative, the spring 55 and the end of wire 51 attached to the spring may be considered to constitute arm 34 of FIG. 1.

Figure 2D:
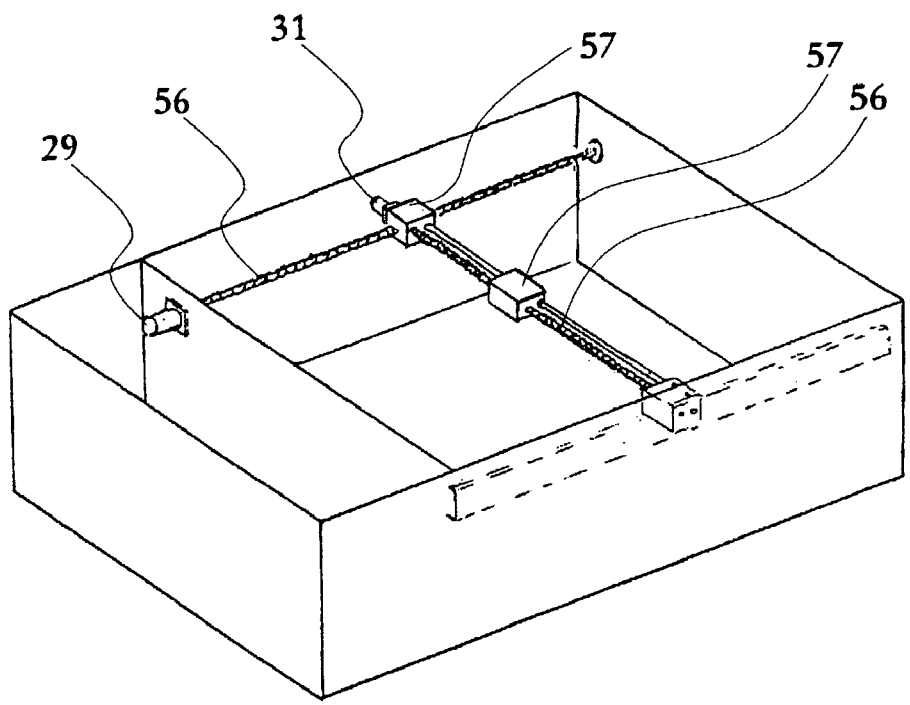

A still further alternative implementation, shown in FIG. 2d, uses a respective rotatable screw 56 and a respective runner 57 for transmission, gearing, and load carrying in the respective direction. In such instance weak step motors may be used.

It shall be appreciated that any combination of the above discussed transmission implementations may be employed. The movements in the X and Y directions have different prerequisites in terms of e.g. available space.

Figure 3:
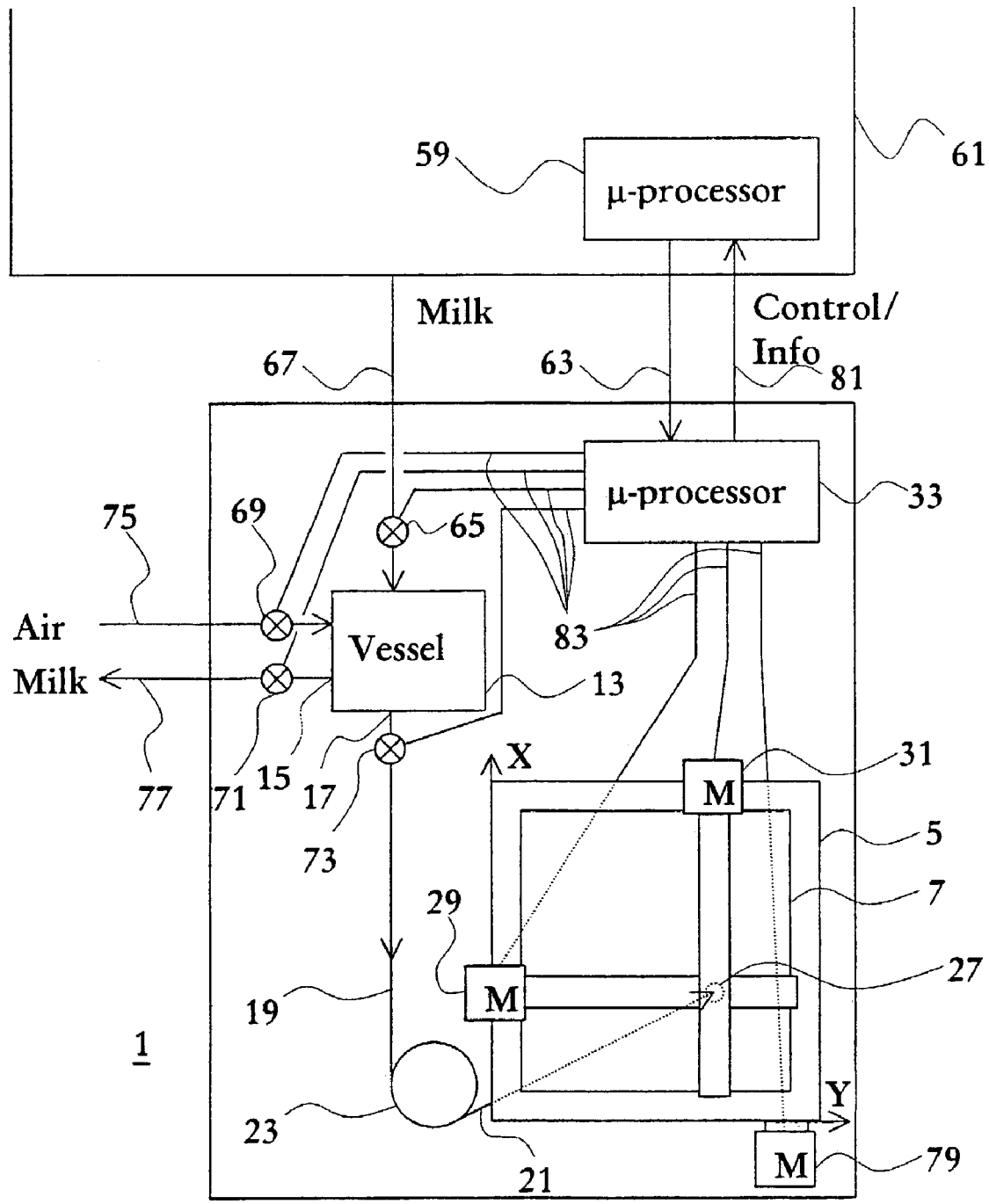
FIG. 3 is a schematic block diagram of an embodiment of the milk sampling apparatus according to the present invention connected to an automated milking system, the sampling apparatus being adapted for two-way communication with the milking system.

Next, with reference to FIG. 3, which is a schematic block diagram of the inventive milk sampling apparatus including a two-way communication interface to the automated milking system, said milk sampling apparatus, and particularly the function thereof, will be further described.

When a sample is to be taken an initiating signal from a processing means 59 of automated milking system 61 is via line 63 sent to processing means 33 of milk sampling apparatus 1 together with XY coordinates for the sample tube to be used for the current sample. Processor 33 sends a control signal to open valve 65 and a representative fraction of milk from a milking is then by way of gravity flowed from automated milking system 61, through conduit 67, and into collection vessel 13. At this point all other valves 69, 71, 73 are closed. Meanwhile processor 33 sends control signals to servo systems 29, 31 instructing them to move filling member 27 to the coordinates as received from automated milking system 61.

Further, when all milk has been flowed into vessel 13 compressed air is supplied to the vessel through line 75 by opening valve 69, which is controlled by processor 33. During the supply of compressed air valve 65 is either opened or closed; in the latter instance the amount of air supplied has to be controlled such that the pressure in collection vessel 13 does not raise unduly much. Line 75 ends inside vessel 13 close to the bottom thereof and by blowing air through the milk it is prevented from being bedded, which would not yield a representative sample.

Next, valve 71 is opened by processor 33 such that a major portion of the milk is evacuated through line 77. The milk left in vessel 13 is given by the cross sectional area of vessel 13 and the height at which outlet 15 is arranged. A typical volume is 8–16 ml. The evacuated milk may be thrown away, recirculated to automated milking system 61, or transported to e.g. a milk storage tank (not shown in FIG. 3).

Valve 71 is closed and valve 73 is opened. At this time the filling member is at place at the given coordinates, i.e. above the selected sample tube. By means of the compressed air the milk sample is flowed out of outlet 17, through a conduit 19 and a hose 21, and out through the orifice of filling member 27, and finally collected in the selected sample tube. The air is blown for a period of time such that it is safeguarded that the entire milk sample has been transferred to the sample tube. The vertical distance between the orifice of filling member 27 and the upper end of the sample tube has to be small enough to secure that the entire milk sample will be collected in the correct tube.

When the sample has been collected, processor 33 sends a signal to a motor 79, which shakes shaking table 5 and thus the sample tubes, see further the description with reference to FIG. 4 below.

Finally microprocessor 33 sends a completion message to automated milking system via line 81.

It shall be appreciated that all valves and all motors are controlled by means of processor 33, which is indicated by control lines 83.

Further, processor 33 is preferably provided with a memory, suitable software and a power supply (not shown in FIG. 3). Also, the motors and valves are power supplied in any suitable manner. Preferably, the milk sampling apparatus is provided with a battery for the supplying of power, and thus no electrical connections have to be made at the installation of the apparatus.

The flexible function of the milk sampling apparatus implies that the filling of the sample tubes may be performed in any order. The filling member may be directly moved to any desired position (in terms of position coordinates) above the cassette. Hence, no undue restriction of the movement of the filling member to predetermined positions along a predetermined path is imposed.

Further, if a single sample tube is to be used also for collecting a second non-consecutive sample, e.g. for sampling a cow a second time some hours later, it is readily done simply by instructing the servo systems of the XY-positioning system to move the filling member to the coordinates in question.

Cleaning of all parts of the milk sampling apparatus 1 that come into contact with milk may easily be performed by using the conventional cleaning of the automated milking system.

By providing a drain outlet below any suitable XY coordinate position and by moving the filling member 27 to this position cleaning is simply performed by opening valves 65 and 73 (and possibly by opening a valve (not shown) at the automated milking station side of conduit 67) and letting the cleaning fluid pass through line 67, vessel 13, lines 19, 21 and filling member 27 and be discharged through said drain outlet. Valve 73 may be repeatedly closed and opened during the cleaning process such that vessel 13 becomes repeatedly entirely filled with cleaning fluid to enhance cleaning of vessel 13. Valve 69 may be opened such that compressed air is mixed with the cleaning fluid and if it is desirable to also clean line 77, valve 71 is opened.

If a more frequent cleaning is desired, e.g. subsequent to each sample being taken out, cleaning fluid may be supplied through line 77 by means of connecting it to a pump and a cleaning fluid supply (not shown in FIG. 3). In order to minimize the distance that the filling member has to transverse in order to reach a drain outlet, drain outlet channels can be arranged along one or more sides of the milk sampling apparatus. If such channels are arranged along all sides filling member 27 has never to be moved more than half the width of the milk sampling apparatus.

Two-way communication between the processor of the automated milking machine and the processor of the milk sampling apparatus according to the present invention is realized through communication bus 63, 81. Connection of this bus and of milk conduit 67 are the only connections that necessarily have to be performed at installation of the milk sampling apparatus. However, also connection of conduit 75 to the source of compressed air is conveniently performed at installation as well as connection of conduit 77 if the milk flowed through this conduit is to be recovered.

Communication from the automated milking station to the milk sample apparatus may preferably include various kinds of control commands and interrogation and information messages, whereas communication in the opposite direction include various kinds of information and alarm messages.

Communication from the automated milking station to the milk sampling apparatus may particularly include any of:
i. Initiation of milk sampling (XY coordinates for the selected sample tube is included in the message).
ii. Initiation of a cleaning cycle, which instructs processor 33 of the milk sampling apparatus to take the steps as described above.
iii. Instructions that automatic cleaning shall be performed after each sample being taken.

Communication from the milk sampling apparatus to the automated milking station may particularly include any of:
i. Information of successful completion of milk sampling.
ii. Electric error alarming message.
iii. Loose cover alarming message.
iv. Erroneously placed sample tube or missing sample tube alarming message.

Various kinds of alarming functions can be arranged by providing the milk sampling apparatus with suitable sensors.

Finally, with reference to FIG. 4, which illustrates an embodiment of shaking table 5 as being part of the milk sampling apparatus 1 of FIG. 1, this aspect of the invention will be described closer.

The sample tubes are typically prepared with a preservative prior to milk sampling, which preservative shall restrain the milk from turning to sour before the samples have been delivered to the laboratory and been analyzed. This preservative is to be dissolved in the milk. Such dissolving typically takes a certain period of time, during which the increase of bacteria in the milk speeds up, and thus the risk that the milk turns to sour increases.

The sample tubes are typically delivered to the farmer in a cleaned and preservative prepared condition. The preservative may be 2-bromo-2-nitropropane-1,3-diol, also widely commercially available under the trademark BRONOPOL, which is crystallized in the bottom of the tubes. The cassette with the prepared sample tubes are typically to be used during a 24 hours period of time, which implies that that the tubes are standing for such a period in the milk sampling apparatus in a milk farm environment without any individual covers. It is under such circumstances desirable to safeguard a fast dissolving of the preservative in the milk. The shaking table 5 of the milk sampling apparatus according to the present invention is thus used to accelerate this dissolving by shaking sample tubes 9.

Figure 4:
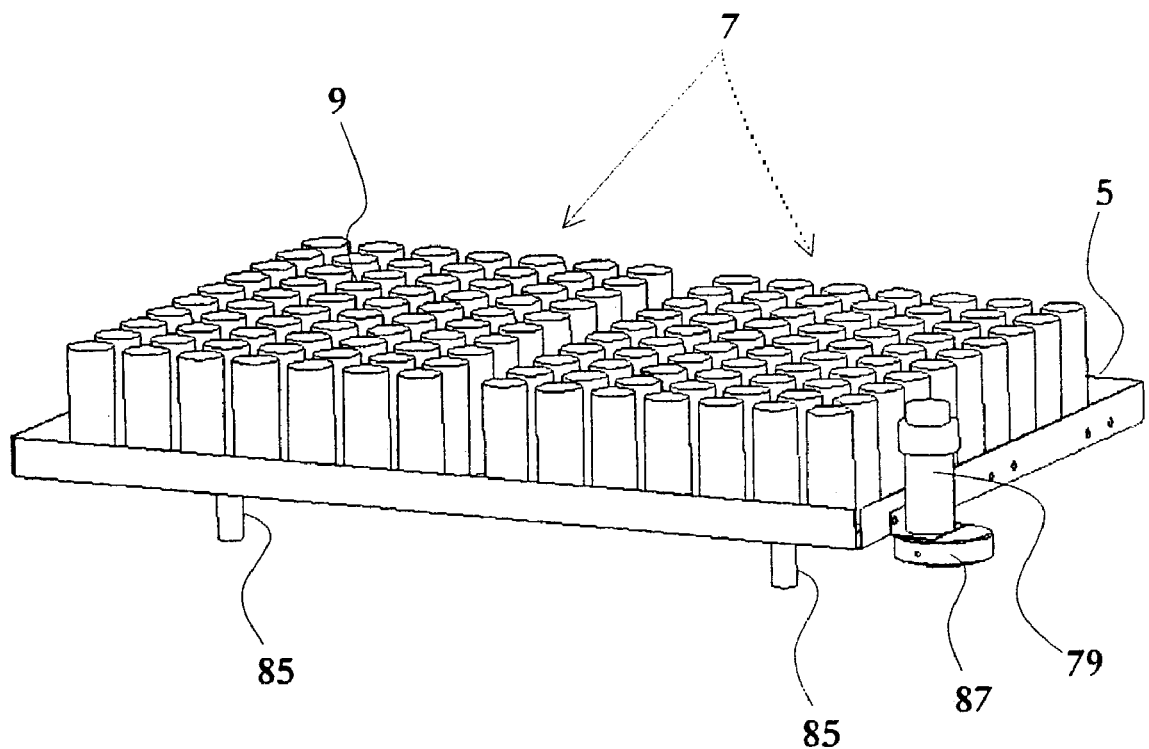
FIG. 4 illustrate an embodiment of a shaking table as being included in the milk sampling apparatus of FIG. 1.

The shaking table in FIG. 4 is arranged on chassis 3 of FIG. 1 by means of four elastic isolator feet 85, preferably made of rubber or plastic, of which only two are indicated in FIG. 4. Two cassettes 7 with sample tubes 9 are arranged on shaking table 5 as schematically illustrated in FIG. 4. The table 5 is being shaken by means of motor 79 rotating an eccentric disk 83. The shaking table 5 can be moved in two transverse directions (X and Y directions) and rotated around a third axis, the Z axis, being perpendicular to X and Y dimensions.

The shaking operation may be affected by the mutual placement of various parts of the milk sampling apparatus such as shaking table, motor, eccentric disk, cassette, sample tubes and elastic isolator feet. Furthermore, the weights and weight distributions of the eccentric disk and of the shaking table may be altered. System constants such as rotation speed of the eccentric disk, spring constant and damping constant of the elastic isolator feet may also be altered. All these parameters affect the shaking function and thus a number of actions may be taken in order to properly design the shaking table to yield an appropriate agitation of the samples. Other shaking tables that may be used in the present invention are disclosed in U.S. Pat. Nos. 4,102,649 and 5,259,672, which patents hereby are incorporated by reference.

If no agitation of the sample tubes is performed, the preservative has partly or completely become dissolved after about an hour, but this may in some applications be a too long period of time since the growth of bacteria has started. By using the shaking table of the present invention the dissolving of preservative in milk is strongly accelerated. Preferably, shaking is performed subsequent to each taken milk sample.

Other dissolving acceleration means may be used as a complement or instead of the shaking table, such as ultrasonic devices or any other suitable agitating means known in the art.

Further, it shall be appreciated that a representative small amount (e.g. 8–16 ml) of milk can be sampled directly from the automated milking system, see e.g. U.S. Pat. No. 5,303, 598. In such version of the present invention collection vessel 13 of FIG. 1 may be dispensed with and a small portion of milk (typically in the order of $10^{-4}$ of the total amount of milk) may be flowed from the automated milking system, through a hose and a filling member, and into a sample tube, preferably during the entire time of the milking of an animal in order to obtain a representative sample.

It will be obvious that the invention may be varied in a plurality of ways. Such variations are not to be regarded as a departure from the scope of the invention. All such modifications as would be obvious to one skilled in the art are intended to be included within the scope of the appended claims.

The invention claimed is:

1. A milk sampling apparatus provided for use with an automated milking system, said apparatus comprising a cassette wherein milk sample collecting elements are placed, and at least one filling member placed above said milk sample collecting elements by a positioning system, and brings milk samples, representatively taken from milk yielded during milking of animals by said automated milking system, into said milk sample collecting elements, wherein said selected milk sample collecting elements are each provided with a preservative, and said milk sampling apparatus includes an agitating device capable of collectively agitating said milk sample collecting elements in connection with the milking of the animals.

2. The apparatus as claimed in claim 1, wherein said agitating device is a shaking table.

3. The apparatus as claimed in claim 2, wherein said shaking table is arranged on a chassis by an elastic isolator support.

4. The apparatus as claimed in claim 2, wherein said shaking table is arranged to be shaken by a motor rotating an eccentric disk.

5. The apparatus as claimed in claim 4, wherein said motor has a variable speed capability.

6. The apparatus as claimed in claim 4, wherein said shaking table, said motor, said eccentric disk, and said elastic isolator support are designed and mutually placed so as to enable an appropriate shaking of said milk samples independently of its position in the cassette.

7. The apparatus as claimed in claim 2, wherein said cassette is removably mounted at said shaking table.

8. The apparatus as claimed in claim 2, wherein said agitating device capable of agitating said milk sample collecting elements includes an ultrasonic device.

9. The milk sampling apparatus as claimed in claim 2, wherein said cassette is held at place on said shaking table by an insert.

10. The milk sampling apparatus as claimed in claim 9, wherein said insert has an opening, in which said cassette fits.

11. The apparatus as claimed in claim 1, wherein said preservative is a 2-bromo-2-nitropropane-1,3-diol.

12. The apparatus as claimed in claim 11, wherein said agitating device is effective to accelerate the dissolving of the preservative in the milk sample collecting elements.

13. The milk sampling apparatus as claimed in claim 1, wherein said positioning system comprises:
an arm extending in a first direction in a plane above said milk sample collecting elements and being movable in a second direction in said plane, said first and second directions being orthogonal;
a first runner for holding said filling member and being movable along said arm; and
a first drive unit and a second drive unit;
said first drive unit being effective to move said arm and said second drive unit being effective to move said first runner such that said filling member is positioned above said selected one of said milk sample collecting elements.

14. The milk sampling apparatus as claimed in claim 13, wherein said first and second drives include a respective servo-operated motor.

15. The milk sampling apparatus as claimed in claim 1, wherein said positioning system is capable of bringing a second non-consecutive milk sample, representatively taken from milk yielded during a second milking of said animal by means of said automated milking system, into said selected one of said milk sample collecting elements.

16. The milk sampling apparatus as claimed in claim 1, further comprising a second cassette in which milk sample collecting elements are placed, and said at least one filling member is capable of being placed above a selected one of said milk sample collecting elements in said second cassette.

17. The milk sampling apparatus as claimed in claim 1, further comprising a drain outlet, wherein said filling member is capable of being placed above said drain outlet by said positioning system, and capable of bringing cleaning fluid into said drain outlet.

18. The milk sampling apparatus as claimed in claim 1, further comprising a processing unit arranged to receive an indication of said selected one of said milk sample collecting elements and to control said positioning system such that said filling member is positioned above said selected one of said milk sample collecting elements.

19. The milk sampling apparatus as claimed in claim 1, further comprising a processing unit arranged for two-way communication with said automated milking system.

20. The milk sampling apparatus as claimed in claim 19, further comprising a sensor connected to said processing unit, wherein said processing unit is arranged for sending an alarm signal to said automated milking system depending on the sensing of said sensor.

21. A method for milk sampling in a milk sampling apparatus comprising a cassette wherein milk sample collecting elements are placed, and at least one filling member movable above said milk sample collecting elements by a positioning system, and capable of bringing milk samples, representatively taken from milk yielded during milking of animals by an automated milking system, into said milk sample collecting elements, said method comprising the steps of:
bringing said milk samples into a selected one of said milk sample collecting elements, said selected milk sample collecting elements are each provided with a preservative; and
collectively agitating said milk sample collecting elements in connection with the milking of the animals.

22. The method as claimed in claim 21, wherein said agitating is performed by a shaking table.

23. The method as claimed in claim 22, wherein said shaking table is arranged to be shaken by a motor rotating an eccentric disk.

24. The method as claimed in claim 23, wherein said shaking table, said motor, said eccentric disk, and an elastic isolator support are designed and arranged so as to enable an appropriate shaking of said milk sample independently of its position in said cassette.

25. The method as claimed in claim 22, wherein said cassette is removably mounted at said shaking table.

26. The method as claimed in claim 21, wherein said agitating is performed by an ultrasonic device.

27. The method as claimed in claim 21, wherein said preservative is a 2-bromo-2-nitropropane-1,3-diol, prior to agitation.

28. The method as claimed in claim 27, wherein said agitation is effective to accelerate the dissolving of the preservative in the milk sample collecting elements.

29. The method as claimed in claim 21, wherein bringing said milk sample into said selected one of said milk sample collecting elements is preceded by the step of:
  moving said filling member to a position above a selected one of said milk sample collecting elements by moving an arm, which extends in a first direction in a plane above said milk sample collecting elements, in a second direction in said plane by a first drive, said first and second directions being orthogonal; and
  moving a first runner holding said filling member along said arm by a second drive.

30. The method as claimed in claim 29, further comprising measuring a parameter of said milk sampling apparatus and sending an alarm signal to said automated milking system depending on said measured parameter.

31. The method as claimed in claim 21, further comprising placing said filling member above a drain outlet by a drive unit, and bringing cleaning fluid into said drain outlet.

32. The method as claimed in claim 21, further comprising receiving an indication of said selected one of said milk sample collecting elements and controlling said positioning system so as to positioning said filling member above said selected one of said milk sample collecting elements.

33. A milk sampling apparatus provided for use with an automated milking system, said apparatus comprising a cassette wherein milk sample collecting elements are placed, and at least one filling member placed above said milk sample collecting elements by a positioning system, and brings milk samples, representatively taken from milk yielded during milking of animals by said automated milking system, into said milk sample collecting elements, wherein said selected milk sample collecting elements are each provided with a preservative, and said milk sampling apparatus includes a shaking device capable of shaking said milk sample collecting elements in connection with the milking of the animals.

34. A method for milk sampling in a milk sampling apparatus comprising a cassette wherein milk sample collecting elements are placed, and at least one filling member movable above said milk sample collecting elements by a positioning system, and capable of bringing milk samples, representatively taken from milk yielded during milking of animals by an automated milking system, into said milk sample collecting elements, said method comprising the steps of:
  bringing said milk samples into a selected one of said milk sample collecting elements, said selected milk sample collecting elements are each provided with a preservative; and
  shaking said milk sample collecting elements in connection with the milking of the animals.

* * * * *